(12) United States Patent
Usui

(10) Patent No.: US 6,488,074 B2
(45) Date of Patent: Dec. 3, 2002

(54) APPARATUS FOR CASTING DENTAL PROSTHESIS

(75) Inventor: Masaki Usui, Kyoto (JP)

(73) Assignee: Denken Co., Ltd., Kyoto (JP)

( * ) Notice: Subject to any disclaimer, the term of this patent is extended or adjusted under 35 U.S.C. 154(b) by 0 days.

(21) Appl. No.: 09/924,089

(22) Filed: Aug. 8, 2001

(65) Prior Publication Data
US 2002/0029864 A1 Mar. 14, 2002

(30) Foreign Application Priority Data
Sep. 14, 2000 (JP) .......................... 2000-279118

(51) Int. Cl.⁷ .............. B22C 9/04; B22C 18/06; B22C 27/04
(52) U.S. Cl. ............... 164/256; 164/259; 164/338.1
(58) Field of Search ............... 164/34, 35, 36, 164/516, 517, 518, 519, 256, 259, 338.1

(56) References Cited
U.S. PATENT DOCUMENTS
6,386,265 B1 * 5/2002 Usui .................... 164/114

FOREIGN PATENT DOCUMENTS
JP    2000-176629    6/2000

* cited by examiner

Primary Examiner—Kuang Y. Lin
(74) Attorney, Agent, or Firm—Oliff & Berridge, PLC

(57) ABSTRACT

The present invention proposes an apparatus for casting dental prosthesis designed to save labor and costly malformations. In a form of the invention, a first arm mechanism 20 for conveying a ring and a second arm mechanism 30 for conveying a crucible are provided to slide along the same guide 27. A ring-placing platform C and a burning unit G are placed across the guide 27, and so are a crucible-placing platform D and a casting unit H. When the arm mechanism 20 places a ring on a lifting stage 44, the lifting stage 44 moves upward to contain the ring in a furnace 41, where the ring is heated to burn off the wax inside. Meanwhile, the arm mechanism 30 places the crucible in a container 50, where alloy ingots are melted. After completing the melting of the alloy ingots and the burning of the ring, the arm mechanism 20 conveys the ring onto the top of the crucible in the container 50. Then, a cover 60 closes the container 50 to constitute a chamber, which is then turned upside-down to carry out the pressure casting. After completing the casting, the ring and the crucible are returned to the platforms C, D by the arm mechanisms 20, 30, respectively.

4 Claims, 17 Drawing Sheets

APPARATUS FOR CASTING DENTAL PROSTHESIS

The present invention relates to a casting apparatus for manufacturing dental prostheses, such as inlay, crown, base, implant, and upper parts of implants, from precious metals or non-precious metals.

BACKGROUND OF THE INVENTION

A loss of some or all of the teeth as a result of caries (tooth decay), periodontal disease or the like, causes not only functional declination in speech and chewing and/or a change in the facial appearance but also a bad influence on the health of the whole body. It is therefore important to undergo treatment as soon as possible in order to restore the missing tooth (or teeth). According to one of the known restoration methods, a metallic casting is put in place of the missing part of the teeth. Dental prostheses for restoring missing parts of teeth, however, cannot be mass-produced because the teeth shape is unique for each patient and further the size and shape of the missing part differs depending on the case. Therefore, it is necessary to manufacture prosthesis having a particular shape depending on the case of each patient. Also, the prosthesis must be manufactured with a high degree of accuracy to provide a correct occlusion. Thus, in the field of dental casting, the lost wax process, which is known for providing a high degree of accuracy of casting, is generally used for obtaining castings that meet the above demands.

FIG. 19 is a flow chart showing the process of dental casting according to the lost wax process. Referring to FIG. 19, the steps of manufacturing prosthesis used for dental treatment are described. First, a dentist takes a negative impression model of the mouth and teeth around the object part of a patient (Step S1). A dental technician pours modeling material, such as gypsum, into the negative impression, and solidifies the material to produce a positive model (Step S2). The dental technician forms a desired type of casting model, such as an inlay or crown, using wax or resin for the positive model (Step S3). A sprue wire for forming a sprue runner is attached to an appropriate part of the casting model with wax or the like (Step S4). After that, the casting model is detached from the positive model, and the free end of the sprue wire is pushed into a crucible former made of rubber (Step S5).

FIG. 20 is a front view of a casting model mounted on a commonly used crucible former. The crucible former 90 has a conical base 91 formed at its center, and a hole 92 for inserting a sprue wire 94 is formed on the top of the conical base 91. The hole 92 is filled with softened wax, and the free end of the sprue wire 94 (to which the casting model 93 is attached) is inserted in the soft wax. When the wax solidifies, the casting model 93 is fixed on the top of the conical base 91 with the sprue wire 94.

A metallic cylindrical ring (not shown) is fitted onto the crucible former 90 so that the casting model 93 is surrounded by the ring, and investment material such as gypsum or phosphate is poured into the metallic ring to conceal the casting model 93 (Step S6).

After the investment material is solidified, the crucible former 90 is removed, the sprue wire 94 is pulled out, and the ring is heated to a high temperature. By heating, the wax inside is burned off, leaving a cavity corresponding to the sprue wire 94 and the casting model 93. Thus, a mold is obtained (Step S7).

When the mold is heated to a preset temperature, molten metal is poured into a reservoir at the top of the mold, which is a conical depression having a shape corresponding to the conical base of the crucible former. The molten metal flows into the cavity through the sprue runner. This is so-called pouring work (Step S8). After the poured metal has cooled down and solidified, the mold is broken to take out the casting inside (Step S9). Then, unnecessary parts such as fringe metals along the sprue runner are removed from the casting, and after-treatments such as sanding the surface of the cast are carried out (Step S10). Thus, the prosthesis is completed.

In general, the above-described manufacturing work is carried out by a dental technician. Conventionally, in the work of Step S7, an electrical furnace, called a "ring furnace", is used to heat the ring to burn off the wax and to heat the mold to a preset temperature. The pouring work of Step S8 is carried out, for example, using a pressure casting apparatus with an inverting casting chamber. An example of this type of casting apparatus is disclosed in Japanese Unexamined Patent Publication No. 2000-176629.

The above type of casting apparatus includes a chamber rotatable within 180 degrees, in which a crucible and a mold are oppositely positioned so that the top of the crucible and the reservoir of the mold face each other. With this casting apparatus, the pouring work is carried out as outlined below. First, posing the crucible with its open top directed upwards, alloy ingots are put in the crucible, and the crucible is heated to melt the alloy. Next, the mold, having been heated to about 800–900° C. (degrees Celsius), is placed above the crucible so that the reservoir is directed downwards. Then, the chamber is closed tightly and evacuated with a vacuum pump. As a result, the pressure in the cavity of the mold decreases. After that, the casting chamber is turned upside-down at a preset timing so that the open top of the crucible is directed downwards. Then, the molten metal in the crucible is poured into the reservoir of the mold. The molten metal closes the sprue gate of the sprue runner, so that the pressure in the cavity of the mold is kept low. After that, the evacuation of the casting chamber is stopped, and pressurized air, inert gas or another kind of gas is supplied to increase the pressure in the chamber. The pressure difference between the chamber and the cavity of the mold forces the molten metal to flow through the sprue runner into the cavity of the mold. Thus, the pouring of the molten metal is completed.

With the above type of casting apparatus, it is necessary to carry out the pouring work immediately after the alloy in the crucible has been melted. This is because keeping the metal in the molten state over an excessive length of time will cause oxidization or other quality changes in the metal, which will make the product defective. Therefore, after the metal has been melted, it is necessary to take out the heated mold from the ring furnace and set it in the casting chamber as soon as possible to start the pouring work as described above. As for the ring furnace, the burning needs to be carried out for one to a few hours at about 700–800° C. of temperature. Therefore, it is necessary to put the ring in the furnace to start the burning at an appropriate timing, calculating back from the timing of pouring the molten metal.

Thus, being required to manufacture various forms of prostheses, dental technicians spend much time and labor carrying out the casting work as described above.

Further, the temperatures and time periods for burning the ring and melting the metal must be appropriately determined depending on the selection of investment material and alloy material, because a desired quality of prosthesis cannot be obtained when the settings are inappropriate.

Conventionally, however, not a few pieces of prosthesis result in being defective (e.g. missing a part) as a result of inappropriately setting the apparatuses, wrong order of work and/or accidental omission of work. This is inevitable when the casting work is manually carried out as described above.

To solve the above problems, the present invention proposes an apparatus for casting dental prosthesis, which greatly improves the efficiency of the casting work while preventing wrong operations in the pouring work.

SUMMARY OF THE INVENTION

Thus the apparatus for casting dental prosthesis according to the present invention includes the following elements:

a) a ring-placing platform on which a cylindrical ring with a casting model of a thermally subliming material concealed inside may be placed;

b) a burning unit including a lifting stage and a furnace for heating the cylindrical ring with the casting model to form a mold, where the furnace covers the top of the lifting stage when the lifting stage is lifted to a preset level;

c) a crucible-placing platform on which a crucible containing a casting material may be placed;

d) a casting unit including a chamber having a cylindrical container rotatable about a horizontal axis and a cover for closing the open top of the container, a cover mechanism for attaching and detaching the cover to and from the top of the container, a heater for supplying heat to the container to melt the casting material in the crucible when the crucible is put in the container and the mold is positioned over the crucible so that the sprue of the mold faces the open top of the crucible, and a chamber driver for rotating the chamber about the horizontal axis after the casting material has been melted;

e) a ring conveyer for holding the ring on the ring-placing platform and conveying the ring onto the lifting stage of the burning unit, for holding the ring after burning and positioning the ring over the crucible contained in the container of the casting unit, and for holding the ring after a casting process and returning the ring to the ring-placing platform;

f) a crucible conveyer for holding the crucible on the crucible-placing platform and conveying the ring into the container of the casting unit, and for taking the crucible out of the container and returning the crucible to the crucible-placing platform; and g) a controller for controlling the burning unit, casting unit, ring conveyer and crucible conveyer so that heating of the ring for a preset time period, heating of the crucible and casting work are performed according to a preset sequence.

With the apparatus according to the present invention, the work is carried out as follows. First, the operator prepares the cylindrical metallic ring with the casting model of a thermally subliming material (wax, for example) concealed inside, and places the ring on the ring-placing platform. Also, the operator places the crucible containing the casting material (alloy ingots, for example) on the crucible-placing platform.

After that, under the control of the controller, the automatic casting operation is conducted as follows. First, the ring conveyer holds the ring on the ring-placing platform and conveys it onto the lifting stage of the burning unit. Then, the lifting stage moves upwards to the preset level to contain the ring in the furnace. In the furnace, the ring is burned for a preset time period to burn off the thermally subliming material and to burn the investment material. Thus, a mold with a cavity corresponding to the molding model is obtained. At a time point earlier than the time point of the completion of the burning by a preset time period, the crucible conveyer holds the crucible on the crucible-placing platform and puts it in the container of the casting unit. The container is heated to maintain the preset temperature, at which the casting material in the crucible melts.

The ring, being burned in the furnace, is ready for use when the casting material is completely melted, and so the ring conveyer conveys the ring with the mold formed inside from the burning unit to a position over the crucible in the container. After the ring is set, the cover mechanism moves the cover to close the container, whereby the chamber is tightly closed. After that, the chamber driver turns the chamber upside-down about the horizontal axis to make the molten casting material flow into the mold. This pouring work can be preferably performed with a pressure control including the following steps: removing the air from the chamber before turning the chamber to establish a low-pressure in the cavity; and increasing the pressure in the chamber to promote a smooth flow of the casting material into the cavity. After the casting material poured into the cavity has solidified, the chamber driver returns the chamber to the original (normal) position. Then the cover mechanism moves the cover to open the container, the ring conveyer conveys the ring to the ring-placing platform and the crucible conveyer conveys the crucible to the crucible platform.

Thus, the apparatus according to the present invention enables an automated process from the burning of the ring to the completion of the casting. All that the operator has to do is to remove the crucible former from the ring after the solidification of the investment material, to prepare a crucible with alloy ingots contained inside and to set the ring and the crucible at preset places in the apparatus. There is no need for the operator to do the troublesome conventional work, such as taking out the ring from the furnace and setting it to the casting apparatus. Thus, the workload of the operator is greatly reduced, so that the working efficiency is improved. Further, the number of defective products due to an incorrect operation or the fault of the operator is greatly decreased.

In a form of the apparatus according to the present invention, each ring conveyer and crucible conveyer includes an arm having a gripper for holding an object; a rotating mechanism for rotating the arm about a vertical axis; a lifting mechanism for vertically moving the arm; and a moving mechanism for moving the arm along a horizontal linear path, where the moving mechanisms of both conveyers commonly include a guide along which the arms are moved. With this construction, it is also preferable to dispose the ring-placing platform and the burning unit across the guide, and to dispose the crucible-placing platform and the casting unit across the guide. This construction provides an effective use of the plane space by virtue of the symmetrical arrangement of the components across the guide.

In another form of the apparatus according to the present invention, the cover mechanism includes a cover-securing mechanism for allowing vertical attaching/detaching movements of the cover when the chamber is in the normal position, while securing the cover to prevent it from falling off the container when the chamber is turned upside-down. The cover-securing mechanism includes a wheel attached to the upper end of the container. The wheel has teeth formed at least at a part of the outer circumference and a stopper projecting from the inner circumference. Plural projections are formed at preset angular intervals around the horizontal axis at a part where the projections engage with the teeth of the wheel. The cover has a notch that comes to the same position as the stopper when the chamber is in the normal position.

With the above construction, when the cover-driver lowers the cover while the chamber is in the normal position, the stopper of the cover passes the notch of the wheel, so that the cover can reach the level where the cover tightly closes the container. In the pouring work, when the chamber is rotated toward the reversed position, the wheel rotates due to the engagement of the teeth with the projections, causing the stopper to be off the notch and press the cover onto the container. Thus, by the above construction, the cover can be securely locked to close the container without using electrical or some other types of driving power source.

BRIEF DESCRIPTION OF THE DRAWINGS

FIG. 3A is a top view and FIG. 3B is the front view.

FIG. 10A is a top view and FIG. 10B is a front view.

FIG. 11A is a top view and FIG. 11B is a front view.

FIG. 12A is a top view and FIG. 12B is a front view.

FIG. 13A is a top view and FIG. 13B is a front view.

DETAILED DESCRIPTION OF A PREFERRED EMBODIMENT

An embodiment of the apparatus according to the present invention is described referring to the attached drawings.

First, the construction of the apparatus 1 of the present embodiment is described.

Figure 1:
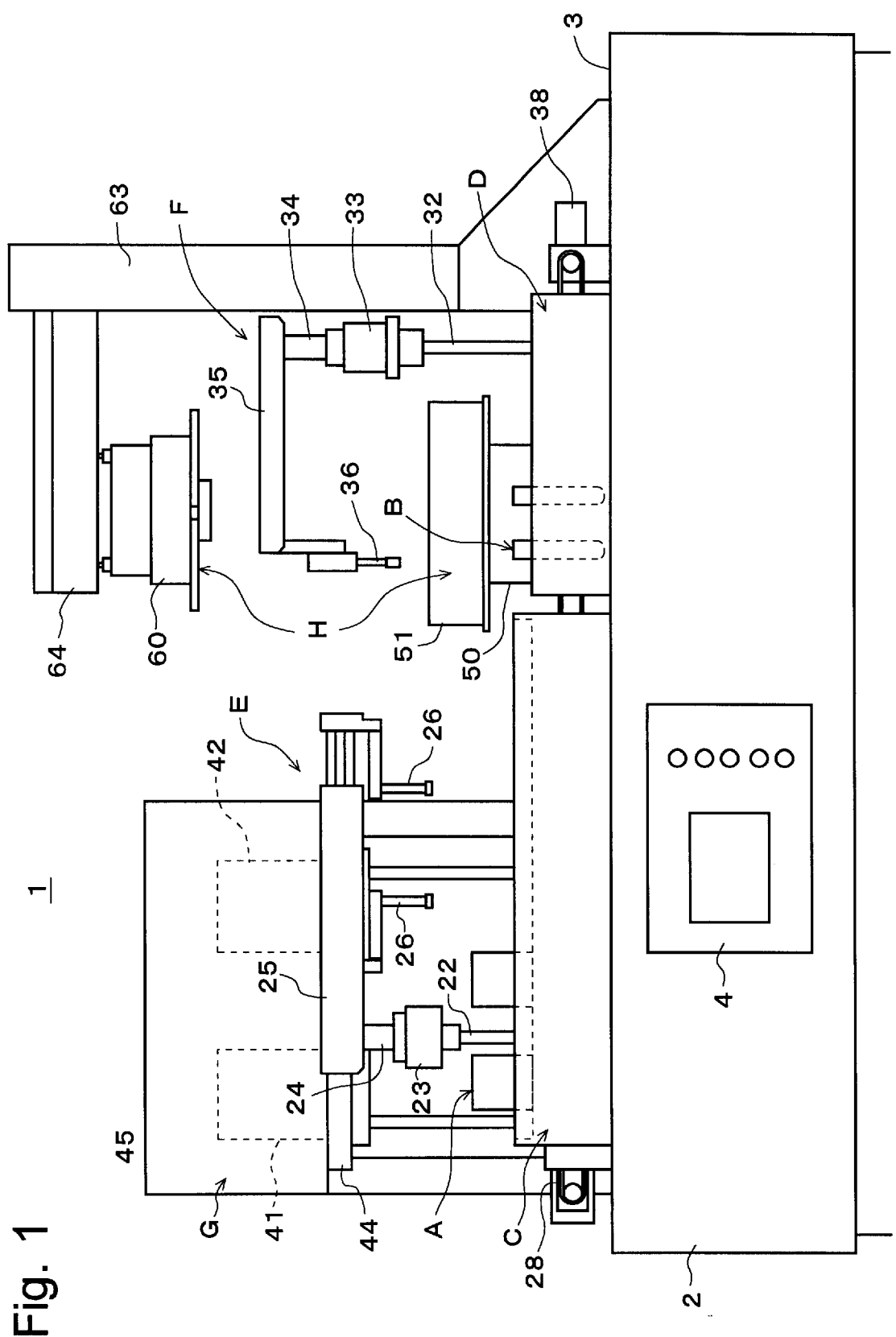
FIG. 1 is a front view of the main part of an apparatus as an embodiment of the present invention.
Figure 2:
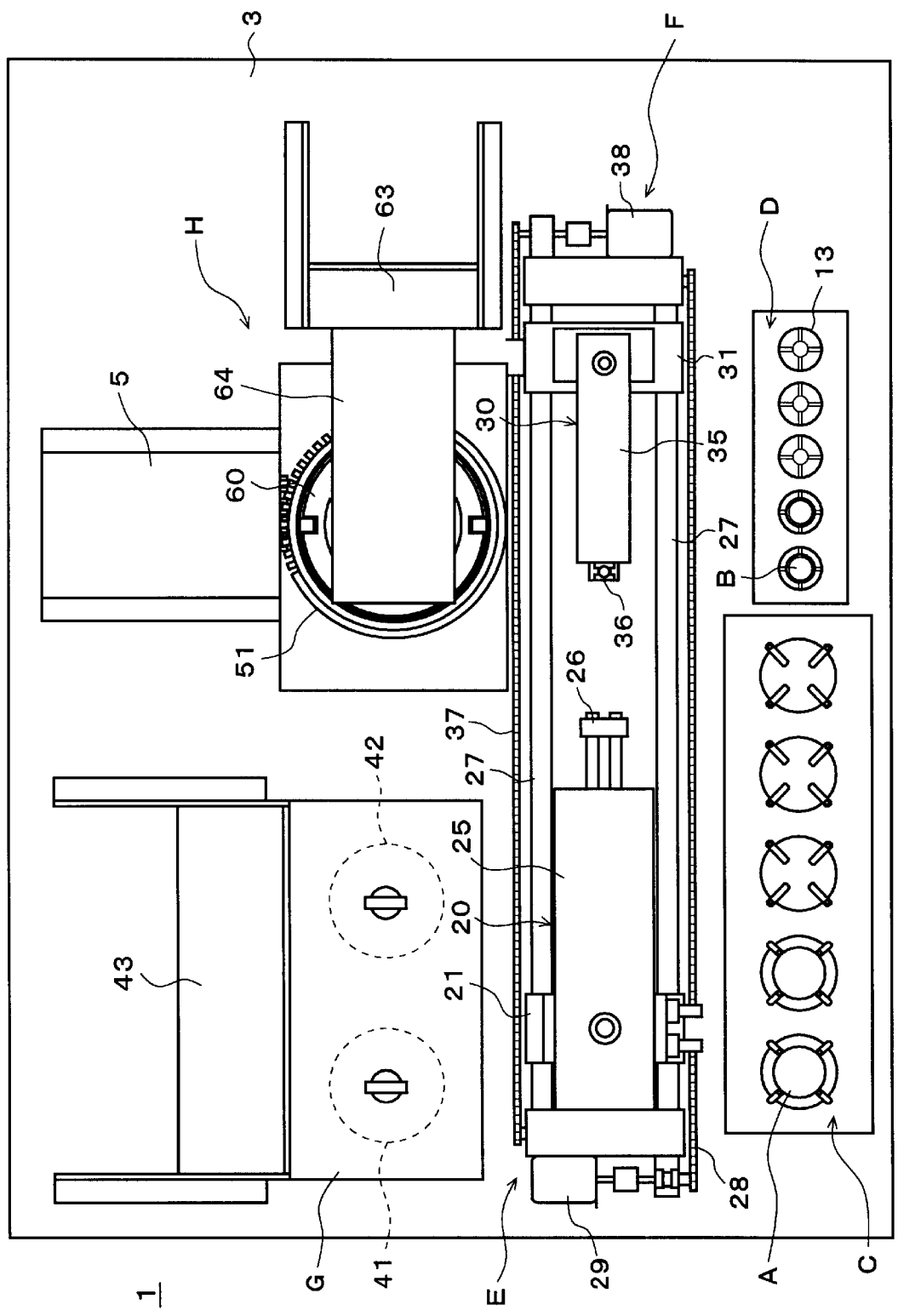
FIG. 2 is a top view of the main part of the apparatus of the embodiment.

Referring to FIGS. 1 and 2, the apparatus 1 has a casing 2 with a table 3 at the top, on which a ring-placing platform C, crucible-placing platform D, ring conveyer E, crucible conveyer F, burning unit G and casting unit H are disposed. The ring-placing platform C has a maximum capacity of five rings A, and the crucible-placing platform D has the maximum capacity of five crucibles B. The ring conveyer E and the crucible conveyer F are constructed to hold and convey the ring A and the crucible B, respectively. The burning unit G is capable of simultaneously heating two pieces of the rings A with independent temperature controls. The casting unit H is operative to heat the crucible B to melt the alloy contained in the crucible B, and to perform the casting work on the ring in which a mold has been formed by burning. The casing 2 encloses a control circuit for controlling the mechanical and electrical operations of the components of the apparatus, and a mechanism for supplying and stopping the compressed air. An operation panel 4 is provided in the upper part of the front of the casing 2, with which the operator can make settings of the apparatus and give commands to the apparatus.

In the following description, the ring A is referred to by different numerals depending on its state. The first state of the ring, obtained by removing the crucible former after the solidification of the investment material, is referred to by numeral A1. The second state of the ring, obtained by heating the ring to burn off the wax, is referred to by numeral A2. Also, the crucible B is referred to by different numerals depending on the state of the alloy contained inside. Numeral B1 is used to denote the crucible containing solid alloy ingots, and numeral B2 is used to denote the crucible containing molten alloy.

The construction and operation of each component of the apparatus is described referring to FIGS. 1 and 2 and further to FIGS. 3–16 disclosing the components in detail.

(1) Ring-placing Platform C

Figure 3A:
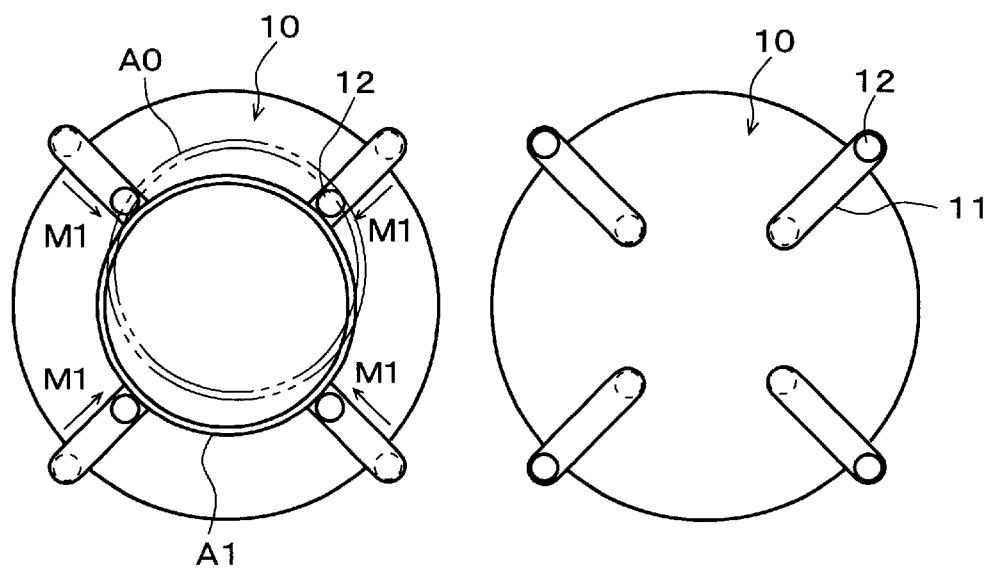
FIGS. 3A and 3B show the details of a part of the ring-placing platform of the embodiment, where
Figure 3B:
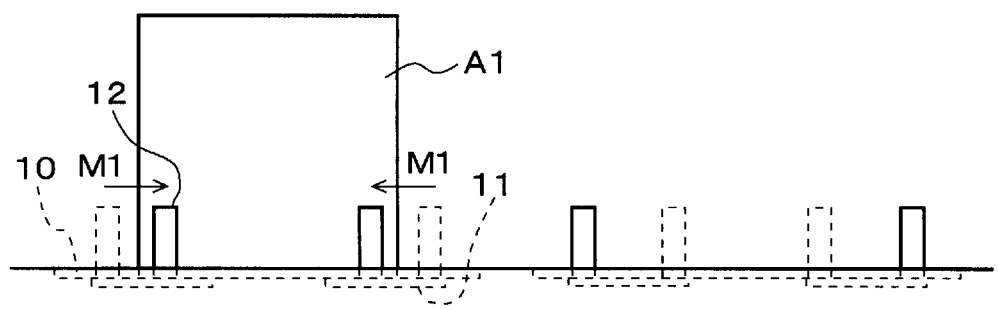

FIGS. 3A and 3B show the detailed construction of part of the ring-placing platform C, where FIG. 3A is a top view and FIG. 3B is a front view. To ensure the holding of the ring with the gripper 26 of the ring conveyer E, which will be described later, the ring-placing platform C is constructed to adjust the position of the ring. That is, the platform C has a slightly depressed circular seat 10, four rectangular holes 11 are radially formed in the seat 10, and four pins 12 are inserted in the holes 11 from below. A pin-driving mechanism (not shown), including an air cylinder, is employed to drive the pins 12 to move along the holes 11 in association with each other.

In an initial phase, or when no ring is placed, the pins 12 are at the outermost positions within the holes 11, as shown in the right part of FIGS. 3A and 3B. After placing the ring on the seat 10, when the operator commands the apparatus to perform a centering operation, the air cylinder actuates the four pins 12 to move simultaneously toward the center of the seat 10 (in the direction M1). Thus, when, for example, the ring is placed at the position A0 as shown in the left part of FIG. 3A, the four pins 12 push the ring to the center of the seat 10. The diameter of the ring is preset large enough to prevent the pin 12 from reaching the innermost position within the hole 11 when the ring is placed on the seat 10.

Thus, the apparatus is equipped with a detection mechanism for detecting the pins 12 at the innermost position. A detection of the pin 12 by the detection mechanism provides a basis for determining that no ring is placed on the seat 10.

(2) Crucible-placing Platform D

The crucible-placing platform D is provided with retention holes 13, each for retaining the crucible B in a standing state, as shown in FIG. 2.

(3) Ring Conveyer E

Figure 4:
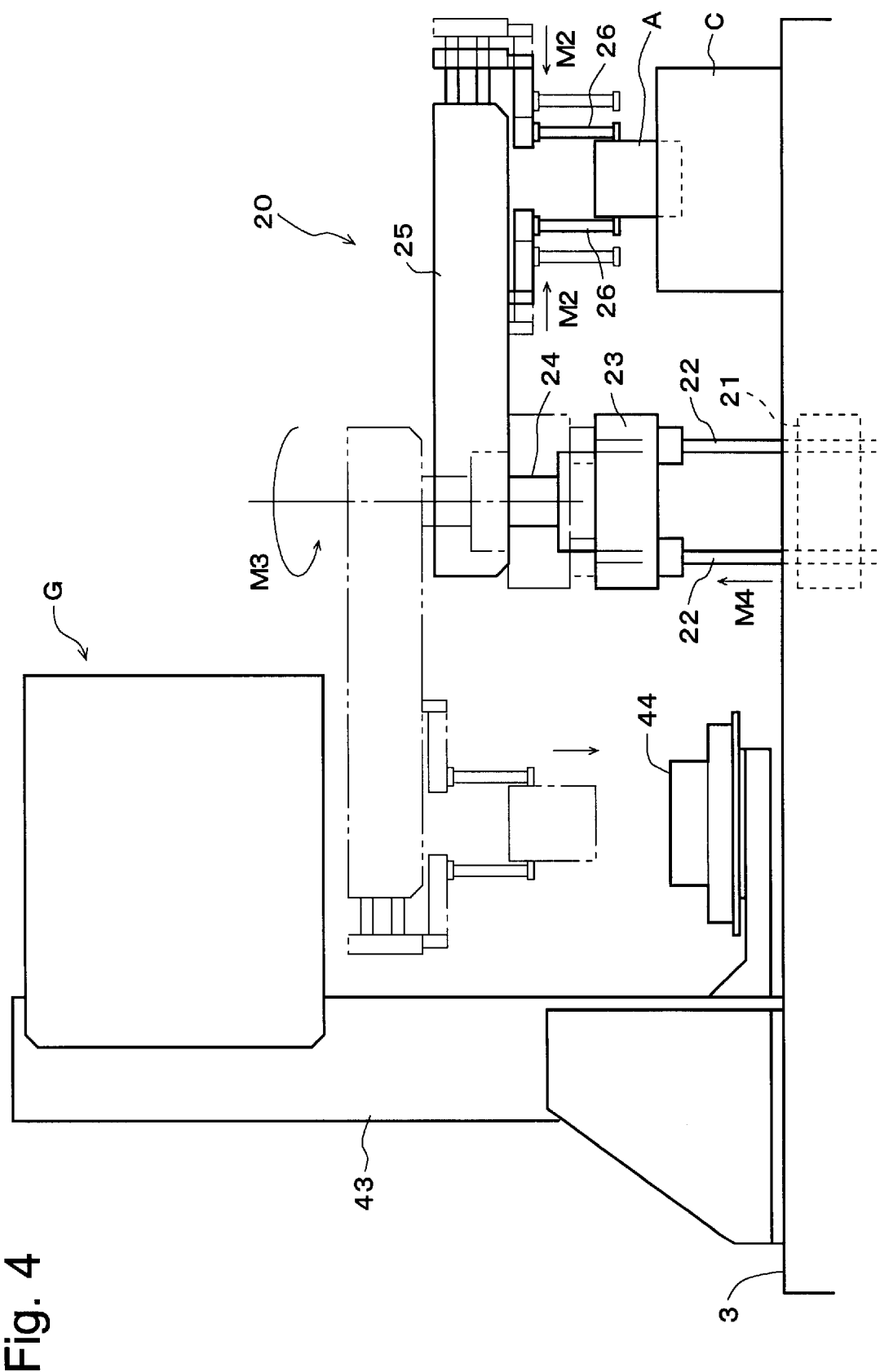
FIG. 4 shows the construction of the ring conveyer E and the burning unit F, as viewed from the left side in FIG. 1.

The ring conveyer E is constructed as shown in FIGS. 1, 2 and 4. FIG. 4 shows the main part of the ring conveyer E, as viewed from the left side in FIG. 1. The ring conveyer E operates as follows. First, the ring conveyer E takes the ring A from the ring-placing platform C one after another and places it on the lifting stages 44, 45 of the burning unit G. Second, the ring conveyer E takes the ring from the lifting stages 44, 45 after the completion of the burning and puts it in the container 50 of the casting unit H. Third, the ring conveyer E takes the ring out of the container 50 after the completion of the casting work and returns it to the ring-placing platform C.

The above operation of the ring conveyer E is performed with an arm mechanism 20. The arm mechanism 20 includes two horizontal guides 27 disposed parallel to each other. A base 21 is sidably mounted on the guides 27. A pair of contraction and expansion legs 22 stand vertically, penetrating the base 21. A support base 23 is fixed to the upper ends of the legs 22. A rotatable main shaft 24 stands upward from the support base 23. An arm 25 is fixed to the upper end of the main shaft 24. A pair of grippers 26 with four fingers are provided at the end of the arm 25. The grippers 26, facing each other, can move along the arm 25 so that they come closer to or go farther from each other. When coming closer to each other, the grippers 26 can grip the outer circumferential wall of the ring. The base 21 is connected to a chain belt 28 driven by a motor 29, so that the base 21 slides along the guides 27 in accordance with the rotation of the motor 29.

(4) Crucible Conveyer F

Figure 6:
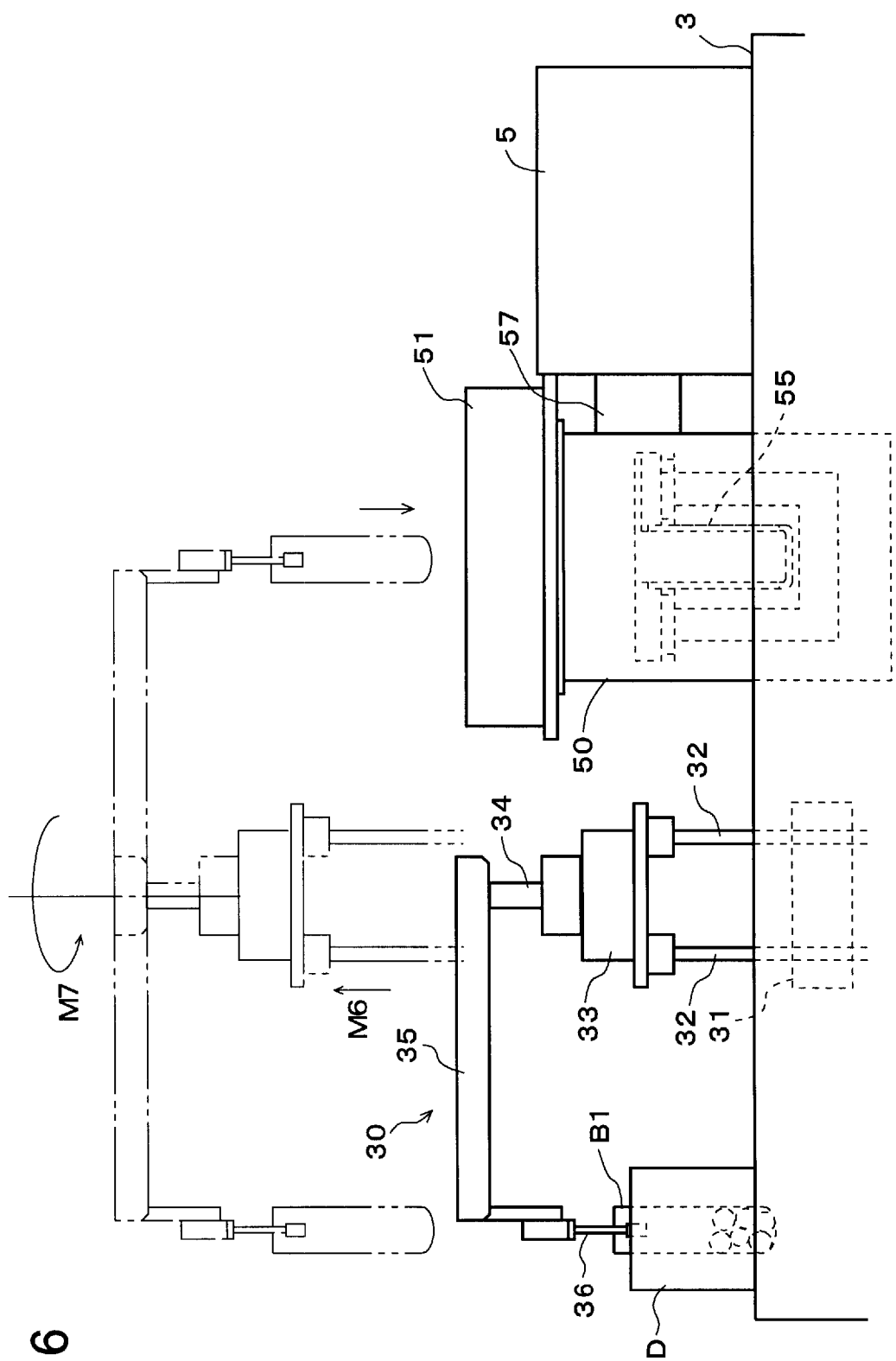
FIG. 6 shows the construction of the crucible conveyer G and the casting unit H, as viewed from the right side in FIG. 1.

The crucible conveyer F is constructed as shown in FIGS. 1, 2 and 6. FIG. 6 shows the main part of the crucible conveyer F, as viewed from the right side in FIG. 1. The crucible conveyer F operates as follows. First, the crucible conveyer F takes the crucible B from the crucible-placing platform one after another and puts it in the container 50 of the casting unit H. Second, the crucible conveyer F takes the crucible B out of the container 50 after the completion of the casting work and returns it to the crucible-placing platform D.

The construction of the arm mechanism 30 of the crucible conveyer F is similar to that of the arm mechanism 20 of the ring conveyer E. That is, the arm mechanism 30 includes a base 31, two legs 32, a support base 33, main shaft 34, arm 35 and a pair of grippers 36 with four fingers. The base 31 is connected to a chain belt 37 driven by a motor 38, so that the base 31 slides along the guides 27 in accordance with the rotation of the motor 38. Thus, the arm mechanisms 20 and 30 are constructed to slide along the guides 27 independent of each other. The grippers 36 of the arm mechanism 30 hold the crucible, where, unlike the grippers 26 of the ring conveyer E, the grippers 36 hold the crucible by inserting the fingers into the crucible B and then moving them apart to press the side wall of the crucible B from inside.

The sliding movements of the arm mechanisms 20, 30 are achieved using the motors 29, 38 as described above. Operations of the other components of the arm mechanisms 20, 30 are achieved with an air motor or an air cylinder using compressed air. For example, contraction and expansion of the legs 22, 32 to vertically move the arms 25, 35, rotation of the main shafts 24, 34 to rotate the arms 25, 35 and hold/release actions of the grippers 26, 36 can be achieved using an air motor or an air cylinder. Driving forces may be of course generated by electrical means or by other types of driving mechanisms.

(5) Burning Unit G

Figure 5:
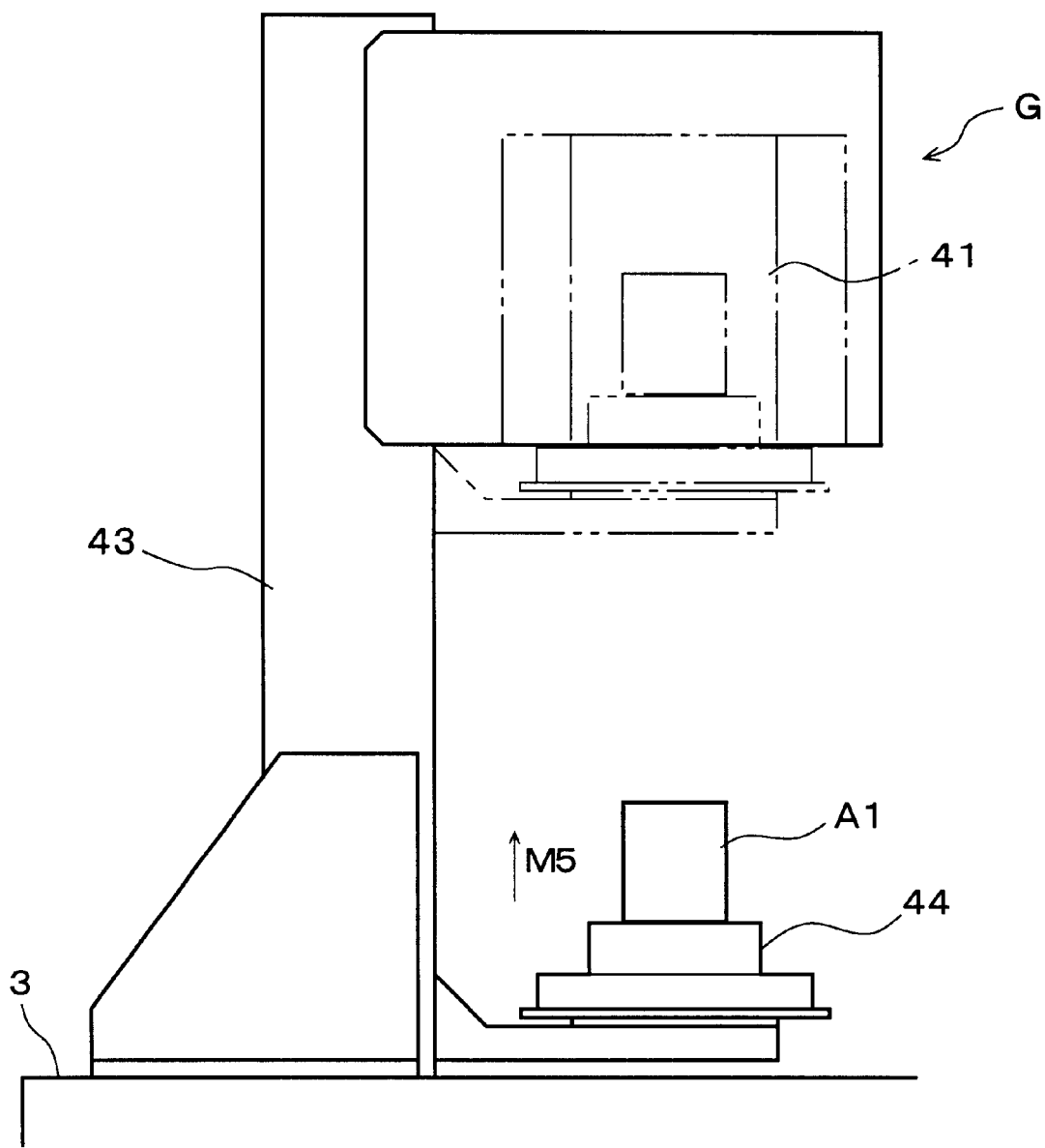
FIG. 5 shows the construction of the burning unit F, as viewed from the left side in FIG. 1.

The burning unit G is constructed as shown in FIGS. 1, 2 and 5. In this unit, two furnaces 41, 42 are placed at the upper end of a stand 43 side by side along the guide 27. Lifting stages 44, 45, which are vertically movable along the stand 43, are disposed beneath the furnaces 41, 42, respectively (FIG. 5 shows only the first lifting stage 44, and the second lifting stage 45 is behind the first one). When the lifting stages 44, 45 are at the highest level, the lifting stages 44, 45 close the bottom openings of the furnaces 41, 42, respectively, and the furnaces are tightly closed.

(6) Casting Unit H

Figure 8:
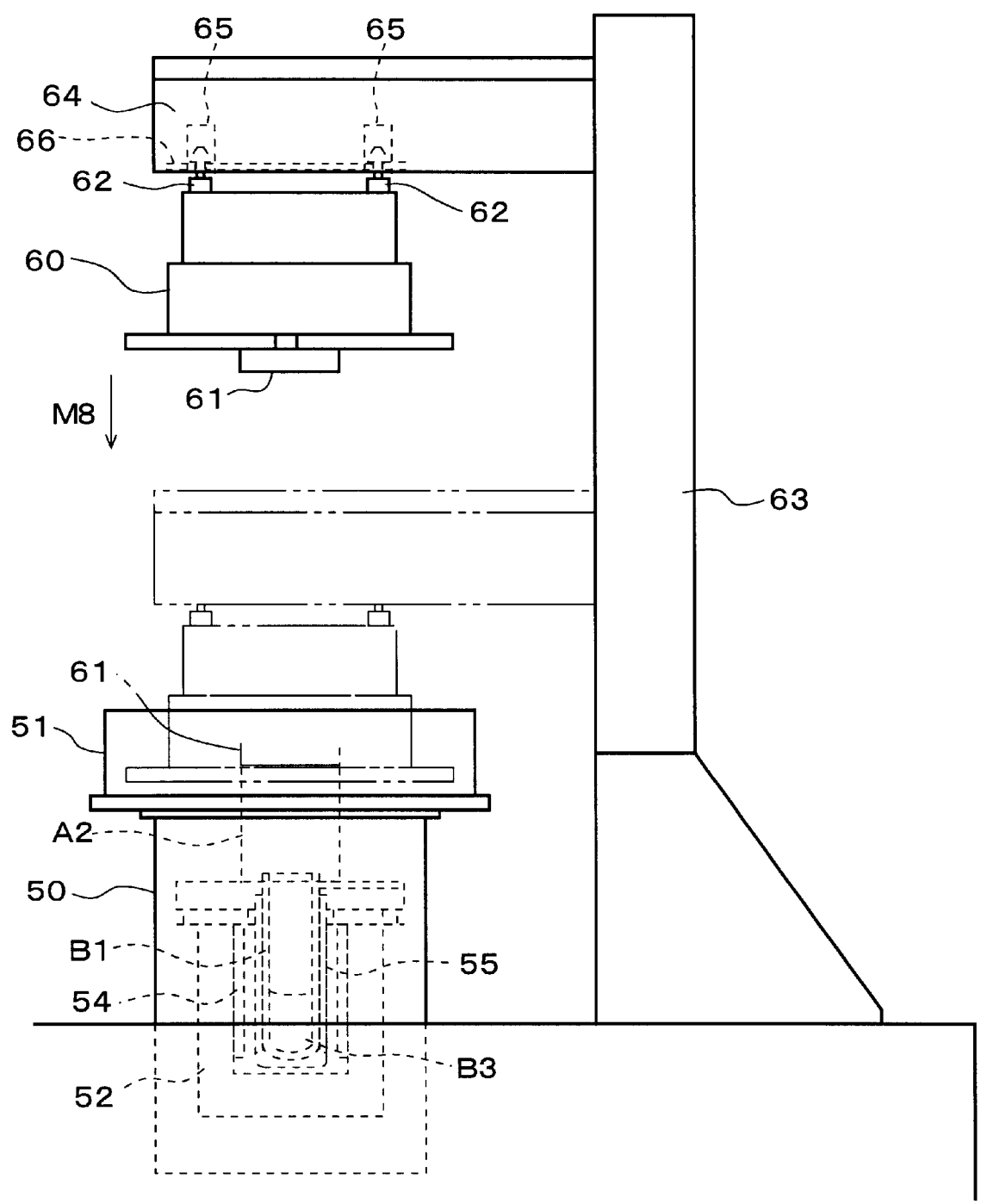
FIG. 8 shows the construction of the casting unit H, as viewed from the right side in FIG. 1.
Figure 9:
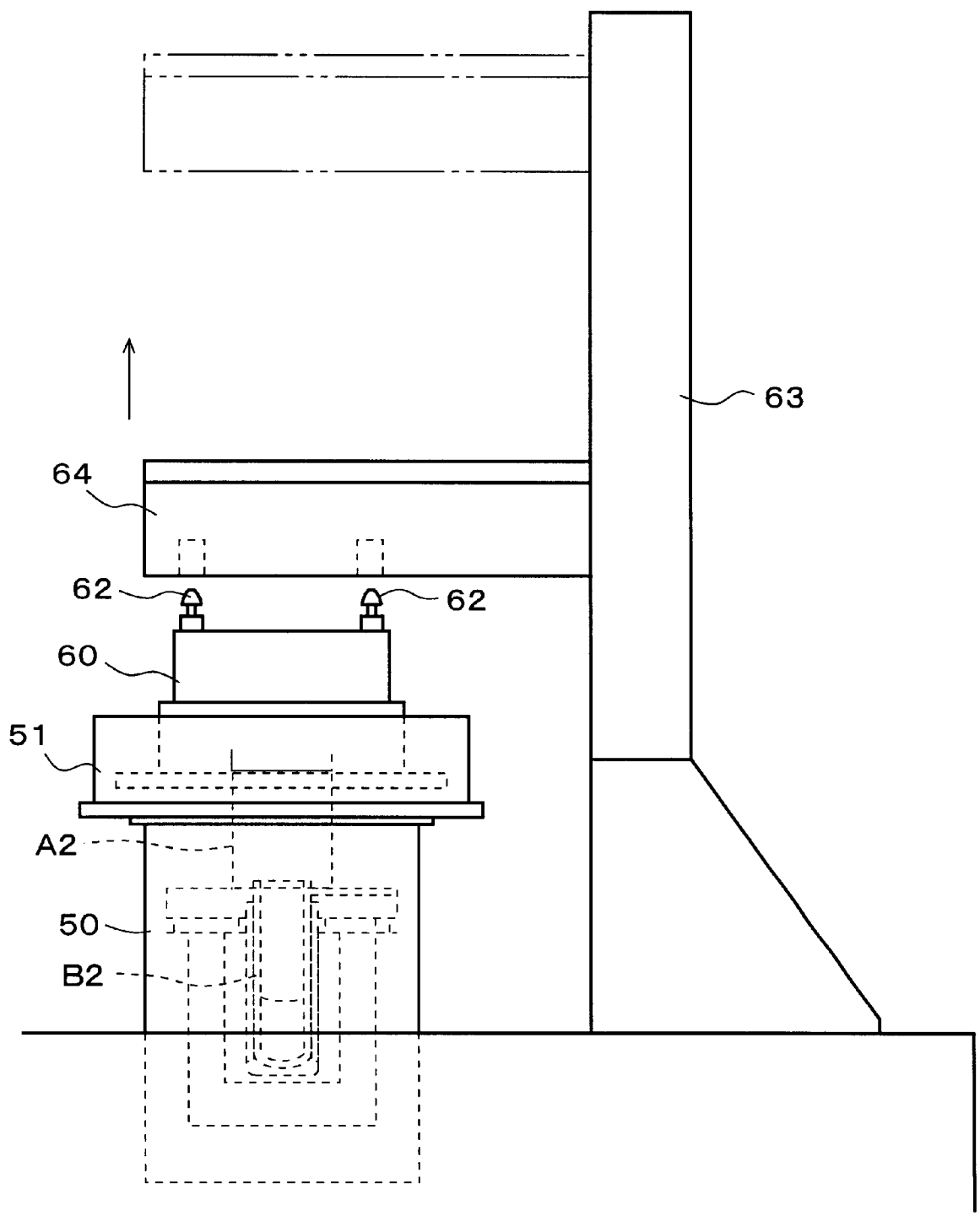
FIG. 9 shows the construction of the casting unit H, as viewed from the right side in FIG. 1.
Figure 15:
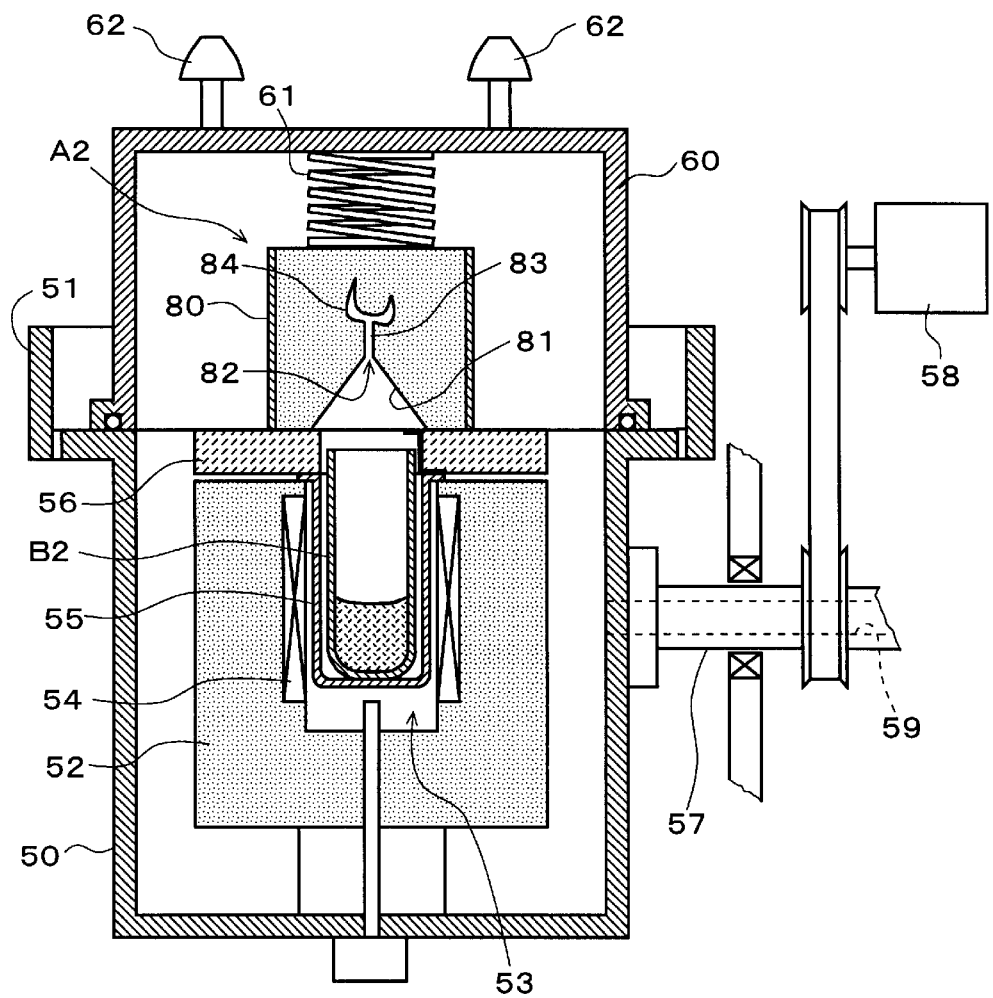
FIG. 15 is a vertical sectional view of the chamber.

The casting unit H is constructed as shown in FIGS. 1, 2, 8, 9 and 15. FIGS. 8 and 9 are front views of the main part of the apparatus 1, and FIG. 15 is a vertical sectional view of the chamber.

The chamber, constructed as a casting furnace, includes a cylindrical container 50 with an open top and a cover 60 that is removably attachable to the open top of the container 50. A wheel 51 is provided at the outside of the upper end of the container 50, slightly leaving a gap from the container 50 to allow the wheel 51 to rotate around the container 50. In the container 50, a support body 52 made of insulating material is disposed, and a heater 54 is circumferentially disposed on the inner side wall of the cylindrical hollow part 53 at the center of the support body 52. A retort 55 made of ceramic with an open top is fitted inside the heater 54. The retort 55 is designed to loosely receive the crucible, allowing its easy removal. The upper end of the retort 55 is formed into a flange extending outwards, and an upper support body 56 made of fire-proofing material is provided to press the flange. This prevents the retort 55 from falling off the hollow part 53 when the chamber is turned upside-down.

A horizontal rotation shaft 57 driven by a motor 58 is fixed to the side of the container 50. The rotation shaft 57 is formed like a tube with one end leading to the inside of the container 50. Thus, the rotation shaft 57 also functions as a gas passage 59 for connecting the inside of the chamber to a vacuum pump and gas inlet valve (both not shown in the figures).

A pressing part 61 at the inner top of the cover 60 includes a coil spring and other elements. With the ring A2 being put in the chamber with the conical reservoir 81 directed downwards, the pressing part 61 pushes down the ring A2 to tighten the connection between the top face of the upper support body 56 and the lower face of the ring A2.

The cover 60 is attachable to and detachable from a cover lifting part 64, which is vertically movable along a stand 63. In detail, the cover 60 is provided with a pair of hooks 62 at the top, and the cover lifting part 64 is provided with a pair of holes 65 in which the hooks 62 are inserted. The cover lifting part 64 is further provided with an engaging plate 66, which is horizontally movable back and forth by means of air cylinder (not shown). With the hooks 62 inserted in the holes 65, when the engaging plate 66 is moved forth, the engaging plate 66 engages with the hooks 62, so that the cover 60 becomes suspended on the cover lifting part 64. When the engaging plate 66 is moved back, the engagement between the engaging plate 66 and the hooks 62 is resolved, allowing removal of the cover 60 from the cover lifting part 64.

In FIG. 9, the casting unit H drawn with the solid lines is in a state where the cover 60 is placed on the top of container 50. In the casting process, the chamber is turned to the reversed position around the rotation shaft 57. In this process, the cover 60 needs to be kept from falling off the container 50. Therefore, the apparatus 1 is equipped with a cover locking mechanism, which will be described below referring to FIGS. 10A–13B.

Figure 10A:
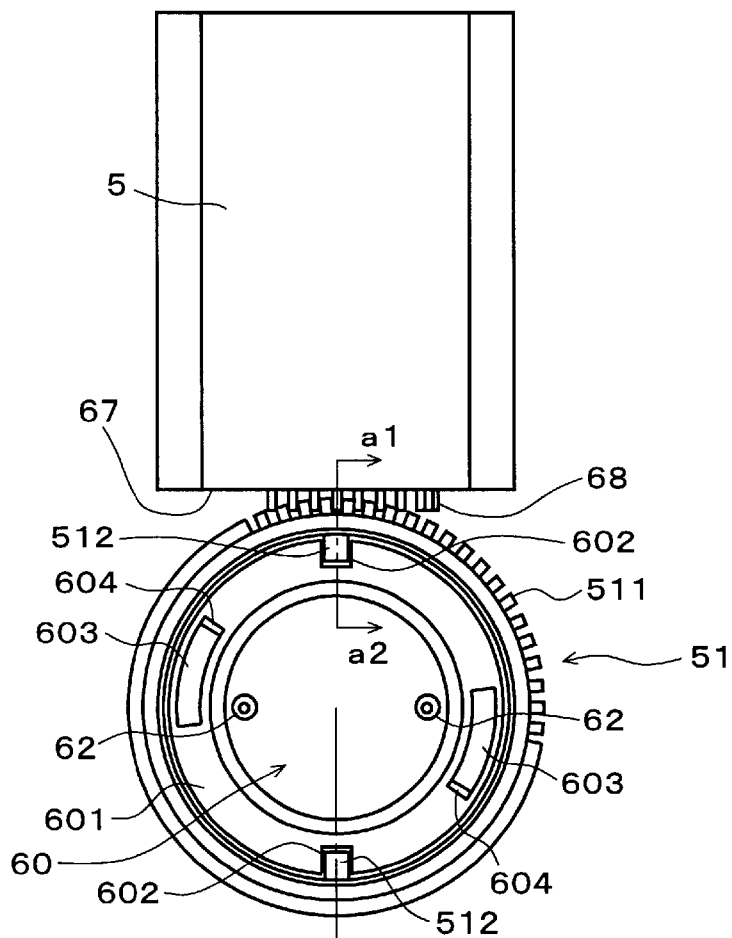
FIGS. 10A and 10B show the chamber of the casting unit H, where
Figure 14A:
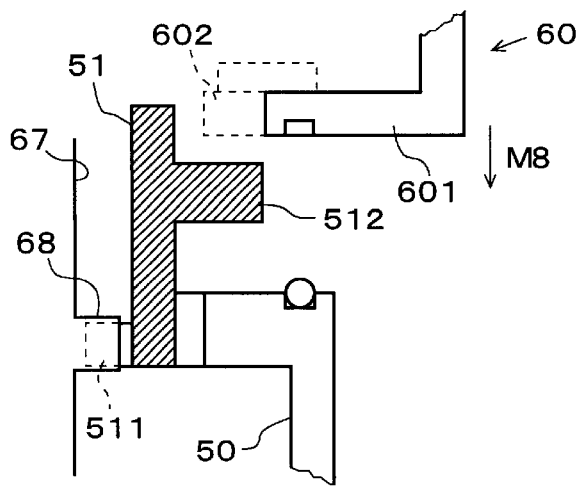
FIGS. 14A–14B show the operations of locking the cover of the chamber.
Figure 14B:
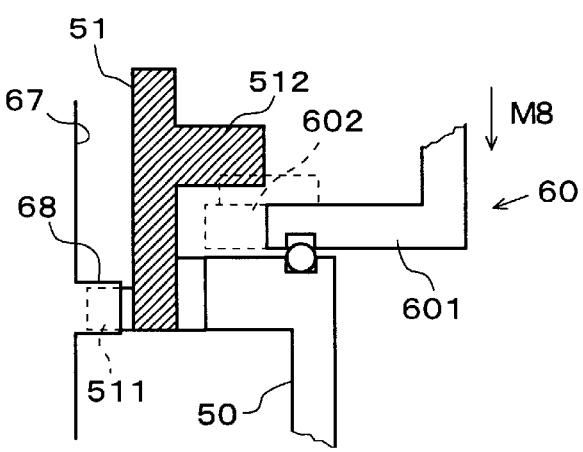
Figure 14C:
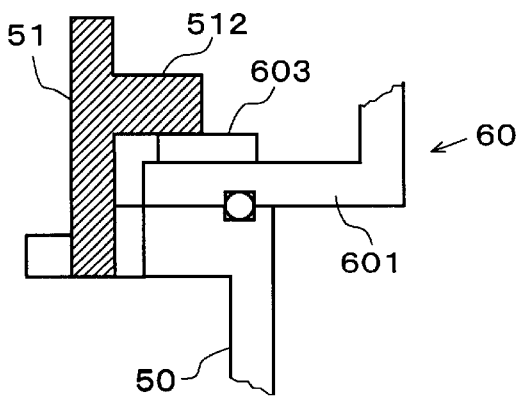
Figure 14D:
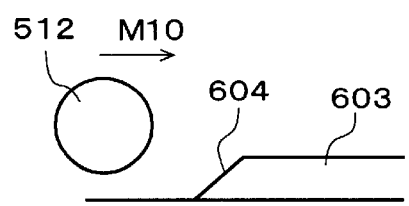

As shown in FIG. 10A, the wheel 51 is provided with teeth 511 formed on the outside of the circumference over a preset angular range, and a pair of pins 512 opposite each other on the inside of the circumference. As for the cover 60, a pair of notches 602 are oppositely formed in the edge of a flange 601 sticking outwards, and a pair of circumferential elevations 603, each having a slope at one end, are oppositely formed on the top of the flange 601, as shown in FIG. 14D. A casing 5 for enclosing the motor 58 and other elements, being fixed to the table 3, has a front wall 67, where plural pins 68 are formed around the rotation shaft 57 to be engaged with the teeth of the wheel 51.

Figure 10B:
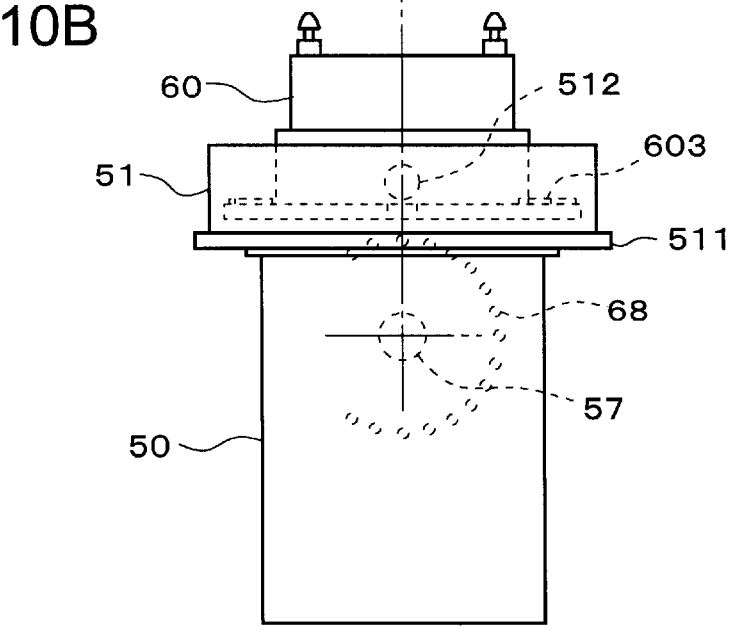
Figure 11A:
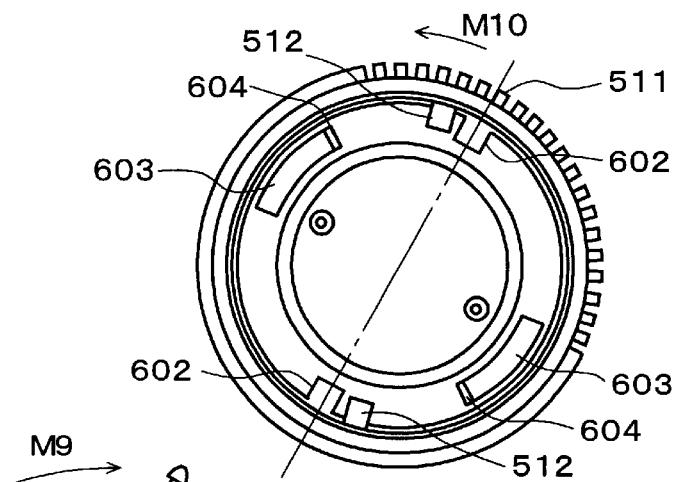
FIGS. 11A and 11B show the chamber of the casting unit H, where
Figure 11B:
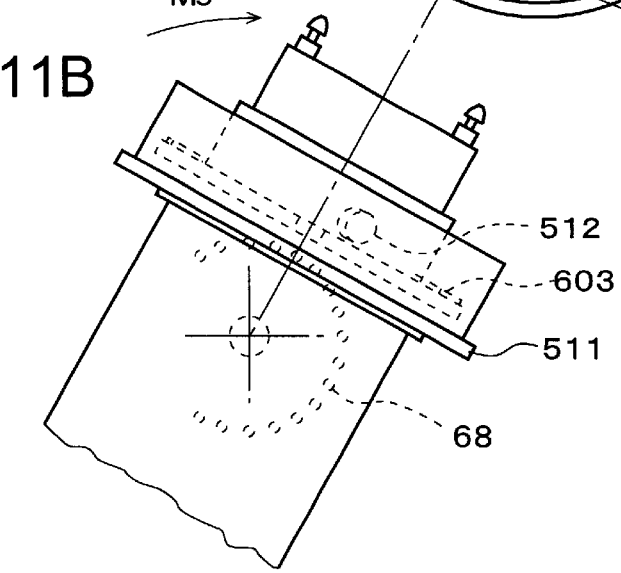
Figure 12A:
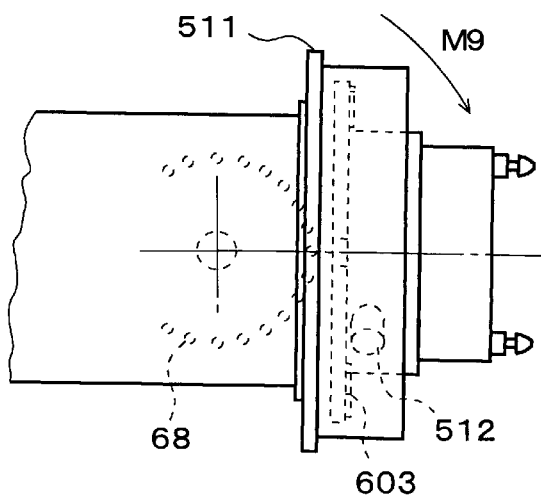
FIGS. 12A and 12B show the chamber of the casting unit H, where
Figure 12B:
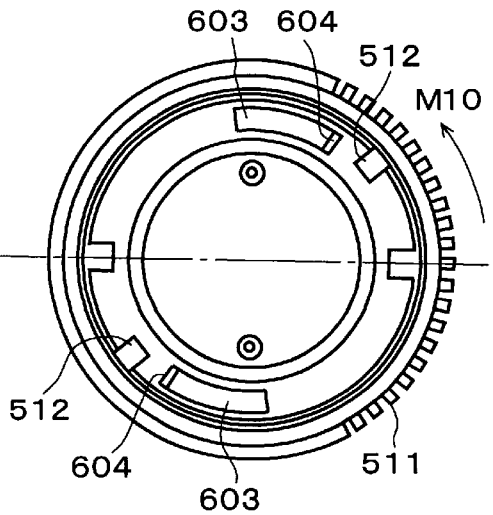

When the chamber is in the normal position, as shown in FIGS. 10A–10B, the notches 602 and the pins 512 are in the same positions. This positioning allows the cover 60 to descend to the level where the cover 60 contacts the container 50, without causing a collision of the flange 601 with the pins 512 (FIGS. 14A, 14B). Starting from the normal position, the chamber is rotated in the direction M9 as shown in FIGS. 11A–12B. During the rotation, the teeth 511, being engaged with the pins 68, receive a force from the pins 68, which causes the wheel 51 to rotate in the direction M10. The cover 60, on the other hand, does not rotate with the wheel 51 because it is tightly pushed onto the container 50 due to the pressure difference. Therefore, in the course of the rotation, the pins 512 of the wheel 51 come off the notches 602 of the cover 60 and move toward the elevations 603, as shown in FIG. 14D.

Figure 13B:
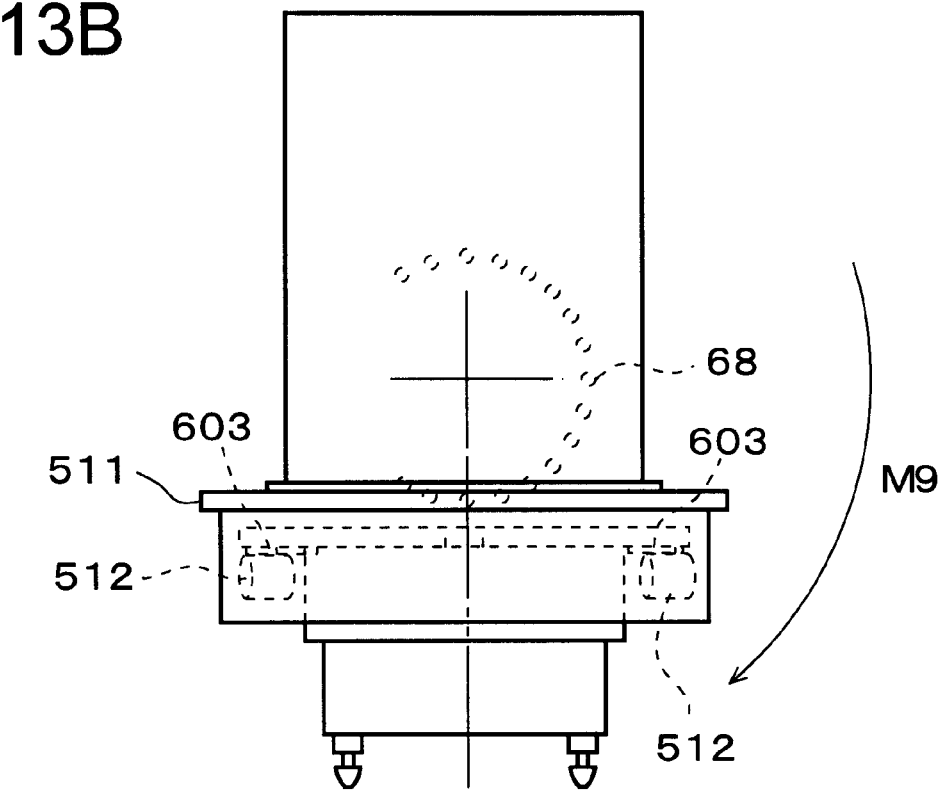
FIGS. 13A and 13B show the chamber of the casting unit H, where
Figure 13A:
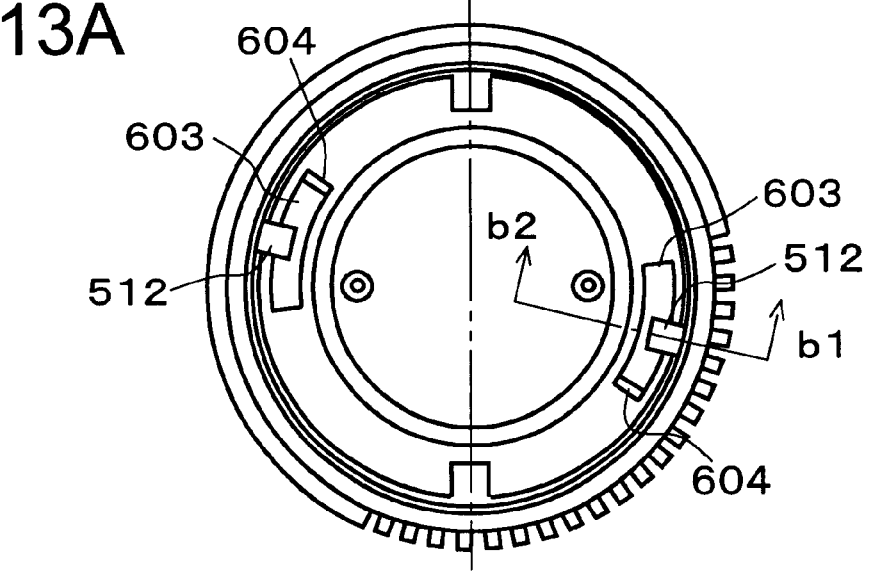
Figure 14E:
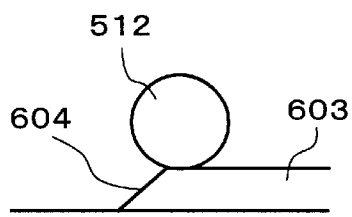

A further rotation of the wheel 51 in accordance with the rotation of the chamber makes the pin 512 climb up the slope 604 of the elevation 603 and then slide along the elevation 603, as shown in FIG. 14E. The pin 512 pushes the cover 60 downwards, as shown FIG. 14C, thus tightening the contact between the container 50 and the cover 60. In this state, the cover 60 is completely prevented from falling off or being displaced even when the chamber is reversed. This is not only because the pins 512 are positioned out of the notches 602, as shown in FIGS. 13A–13B, but also because the elevation 603 increases the friction between the cover 60 and the pin 512. Thus, the cover 60 is maintained in tight contact with the container 50.

As described above, the apparatus 1 of this embodiment is equipped with the mechanism for tightening the contact between the cover 60 and the container 50 in accordance with the rotational position of the chamber without using a special power source such as a motor. When the cover 60 is secured to the container 50, the inside of the chamber is maintained airtight, and the chamber can stand the inner pressure of 1 MPa or above (relative value to the normal atmospheric pressure defined as zero MPa).

When the chamber is in the normal position, as shown in FIGS. 10A–10B, the notches 602 of the cover 60 and the pins 512 are at the same position, so that the cover 60 is allowed to move vertically to be attached to and detached from the container 50. A slight inclination of the chamber, however, causes a collision between the flange 601 of the cover 60 and the pins 512, which obstructs the attachment and detachment of the cover 60. Therefore, the apparatus 1 is provided with a positioning mechanism for correcting the discrepancy in the position (or inclination) of the chamber to maintain it in the normal position.

Figure 16A:
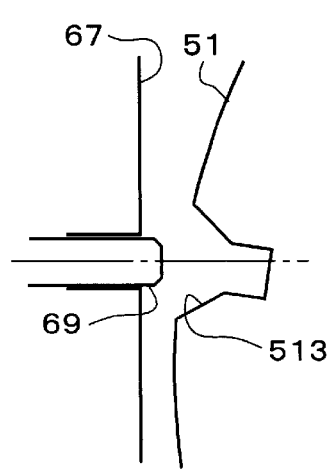
FIGS. 16A and 16B show a positioning mechanism for correcting the position of the chamber.
Figure 16B:
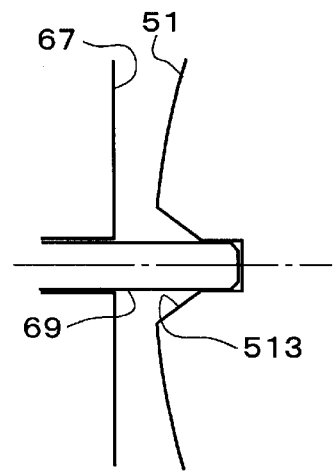

FIGS. 16A–16B show the positioning mechanism, as viewed from above the chamber. The positioning mechanism includes a rod 69 held by the front wall of the casing 5 in such a manner that the rod 69 can move back and forth. The wheel 51 of the container 50, on the other hand, has a bore 513 for receiving the rod 69. In FIG. 16A, the container 50 is slightly inclined about the horizontal axis. When the cover 60 is to be attached to or detached from the container 50, the chamber can be easily maintained in the correct (normal) position by moving the rod 69 forth to reach the bottom of the bore 513, as shown in FIG. 16B.

The operation of the apparatus of the present invention is described below according to the working sequence.

Figure 17:
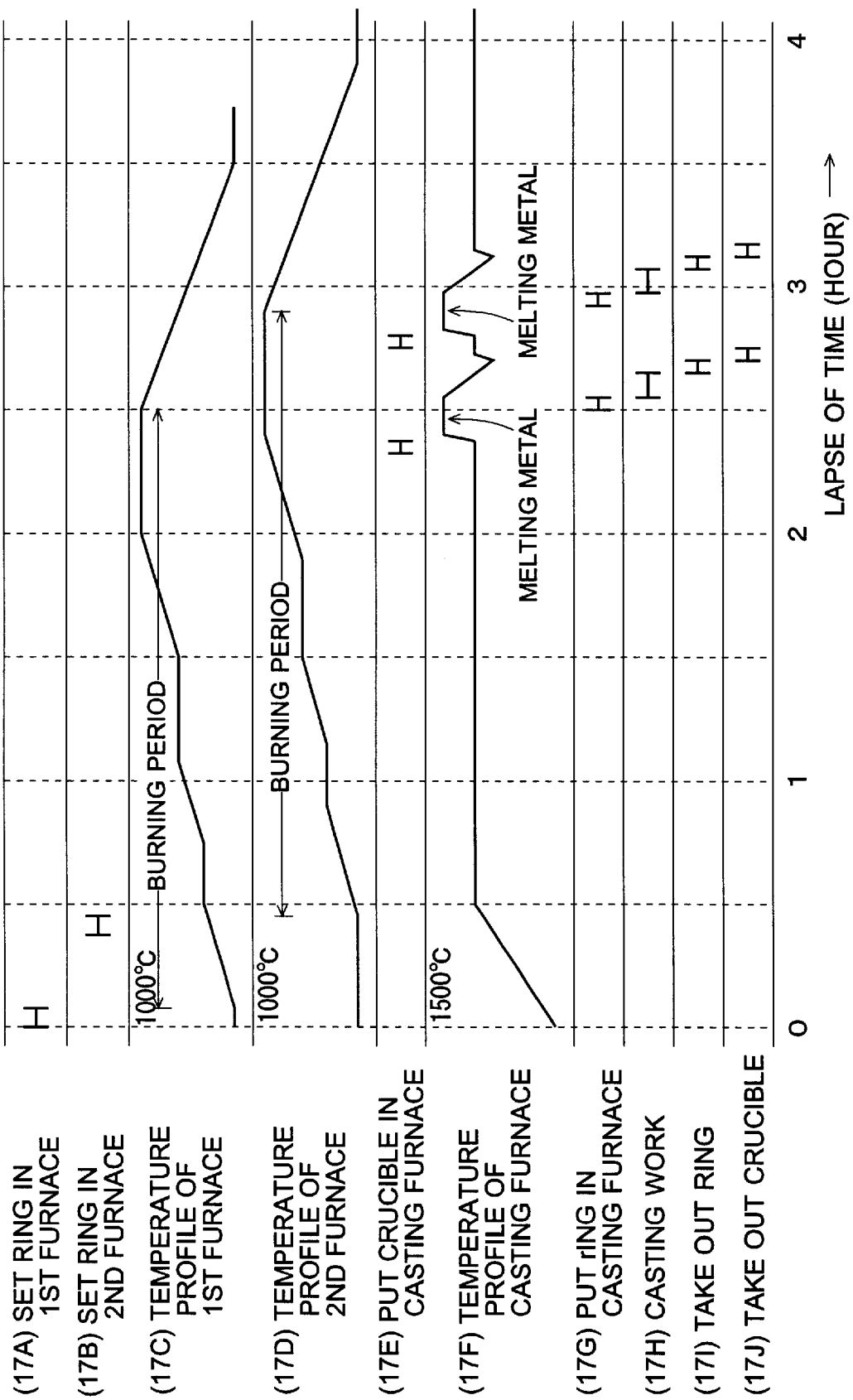
FIG. 17 is a control sequence diagram of the apparatus of the embodiment.
Figure 18:
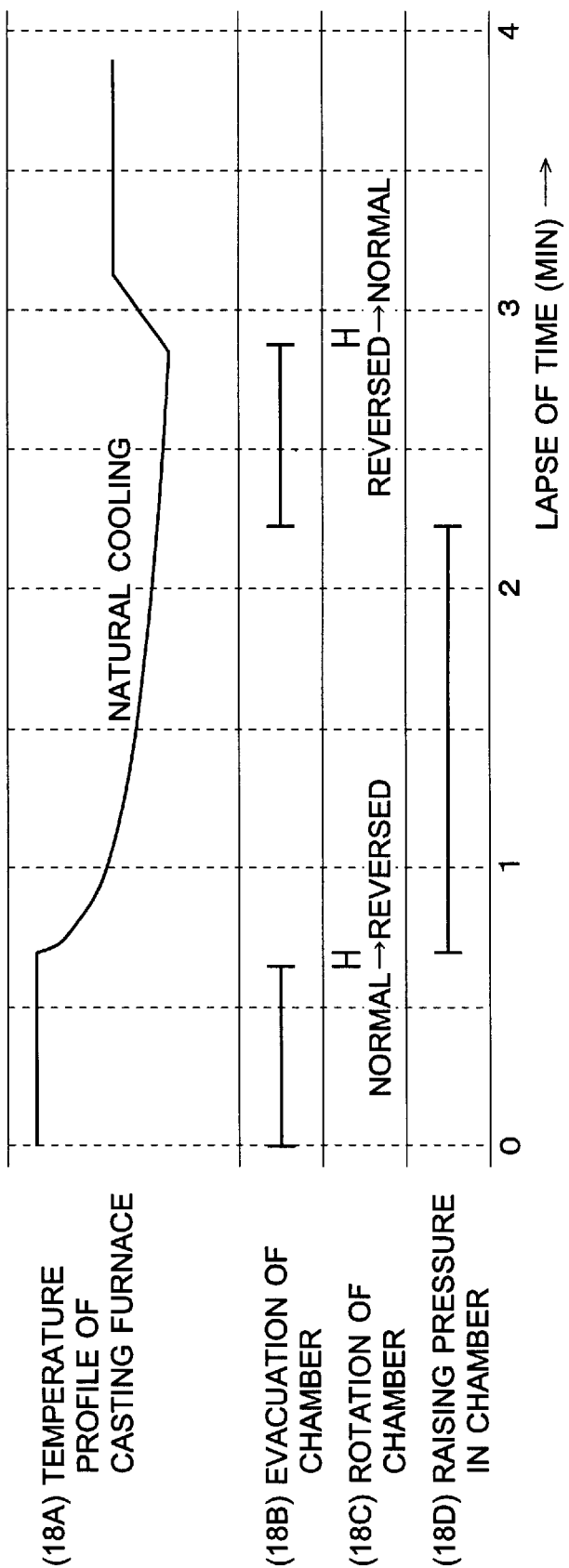
FIG. 18 is a control sequence diagram of the apparatus of the embodiment.
Figure 19:
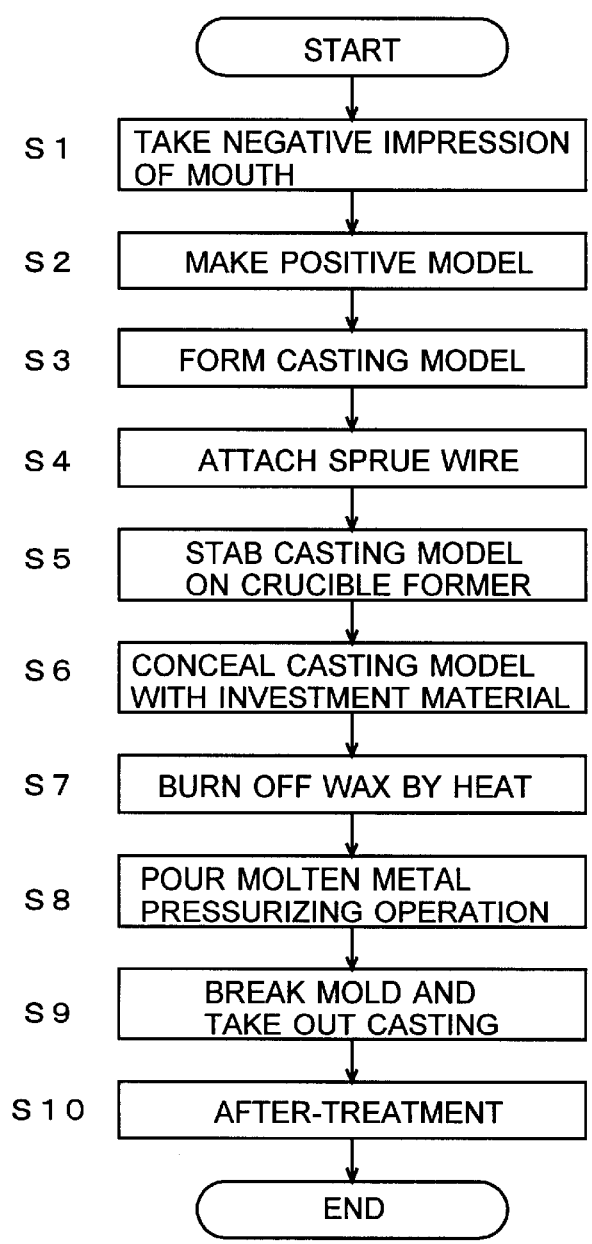
FIG. 19 is a flowchart showing the process steps of casting dental prosthesis by lost wax process.
Figure 20:
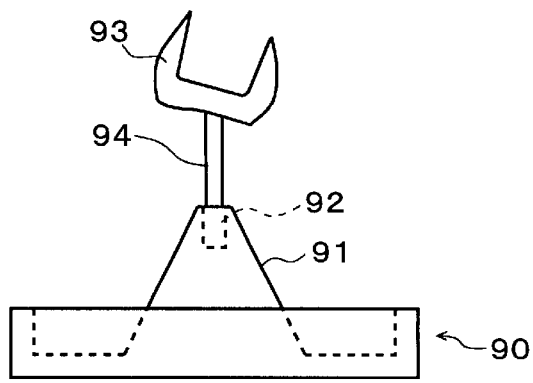
FIG. 20 shows a casting model pushed into a generally used crucible former.

First, the ring A1, manufactured by Steps S1–S6, for example, is placed on the ring-placing platform C. The ring-placing platform C has maximum capacity of five rings A1. Next, the same number of crucibles B1 containing casting material (metal ingots) corresponding to the ring A1 are placed on the crucible-placing platform D. The placements of the ring A1 and the crucible B1 need not be carried out at the same time so long as each of them is already on the platform when needed. In the following description, the number of the rings to be processed is assumed as two. FIG. 17 is a chart showing an example of the control sequence, and FIG. 18 is a chart showing the detailed control sequence of the casting process in FIG. 17.

Before commanding the apparatus to start operating, the operator sets the casting conditions through the operation panel 4. This apparatus has a built-in database holding information about investment materials and casting materials generally used for dental casting with temperature profiles suitable for the materials, so that the operator has only to select the name of the material to set appropriate casting conditions. Further, the operator is allowed to manually set the detailed conditions and store the condition data in the apparatus to use it in the next and/or subsequent casting work.

In response to the switching operation by the operator, the operation panel 4 sends an operation-initiating command to the control circuit, and the control circuit controls the ring conveyer E to convey the first piece of ring. First, the pins 12 of the seat 10 at the first position are driven to move inwards, as shown in FIG. 3, whereby the ring A1 is correctly placed at the center.

After that, the motor 29 is energized to drive the chain belt 28, whereby the ring conveyer E is moved so that the arm mechanism 20 comes to a preset position. In a preferable case, the first arm mechanism 20 is initially at the leftmost position and the second arm mechanism 30 is at the rightmost position in FIGS. 1 and 2, for example. At this time, the grippers 26 of the arm mechanism 20 are fully opened. Then, the arm 25 is rotated until the grippers 26 come directly above the ring A1. After that, the arm 25 is lowered to a preset level, and the grippers 26 are moved in the direction M2 in FIG. 4 to narrow the space between them so that they hold the ring A1. After that, the legs 22 are expanded in the direction M4 in FIG. 4 to lift the arm 25, and then the arm 25 is rotated around the main shaft 24 by angle of about 180 degrees (in the direction M3 in FIG. 4). The arm 25 further moves along the guide 27 to a preset position, if necessary, and places the ring A1 on the lifting stage 44 of the burning unit G (the lifting stage 44 is at the lowest level at this time). After that, the arm 25 is rotated away from the lifting stage 44.

Starting from the state where the ring A1 is placed on the lifting stage 44 as drawn with the solid lines in FIG. 5, the lifting stage 44 moves upwards (in the direction M5 in FIG. 5) to contain the ring A1 in the furnace 41, closing the bottom opening of the furnace 41. After that, the heater (not shown) of the furnace 41 is supplied with the electric current to raise the temperature according to the preset temperature profile. In concrete, the temperature is increased incrementally to 700–900° C. in about two hours, as shown in FIG. 17 (numeral 17C).

After conveying the first piece of ring A1 to the furnace 41 as described above, the ring conveyer E stands by for a preset time period, and then resumes the operation to convey the second piece of ring A1 to the second furnace 42 in the same manner. With the ring A1 contained inside, the second furnace 42 is heated according to the same temperature profile as the first furnace 41, provided that the burning condition of the both furnaces is the same. It should be noted that different temperature profiles should be applied when, for example, different investment materials are used.

As a result of the burning, the wax concealed in the investment material in the ring A1 is burned off, and a mold having a cavity corresponding to the casting model is obtained. The ring, now referred to by numeral A2, includes a cylindrical metallic ring 80 covering the side of the ring. Inside the ring A2, the sprue runner 83 that leads to the sprue gate 82 at the vertex of the conical reservoir 81, and the cavity 84 corresponding to the casting model, are formed, as shown in FIG. 15.

While the ring is being burned in the furnace 41 as described above, the crucible conveyer F conveys the crucible Bi with which the next casting work is carried out into the container 50 of the casting unit H. That is, the motor 38 is energized to drive the chain belt 37, whereby the arm mechanism 30 is moved along the guide 27 to a preset position. Then, after being rotated, the arm 35 is lowered to a preset level where the lower ends 6f the grippers 36 are inserted into the crucible B1 placed on the crucible-placing platform D, and the grippers 36 are moved to widen the space between them so that they hold the crucible B1. After that, the legs 32 are expanded in the direction M6 in FIG. 6 to lift the arm 35, and then the arm 35 is rotated around the main shaft 34 by angle of about 180 degrees (in the direction M7 in FIG. 6). The arm 35 further moves along the guide 27 to a preset position, if necessary, and puts the crucible B1 into the retort 55 in the container 50 of the chamber (FIG. 6).

The heater 54 of the chamber is supplied with the electric current from the beginning of the operation, as shown in FIG. 17 (numeral 17F), and the temperature is stabilized at a preset value when the crucible B1 is put in the container 50. When the crucible B1 is put in the container 50, the electric current to the heater 54 is increased to raise the temperature to a value where the metal is adequately melted (about 1000° C. for precious metal and 1400° C. for non-precious metal). The temperature is maintained for a preset time period, during which the ingots in the crucible are melted into a liquefied state.

Meanwhile, the arm mechanism 30, having finished conveying the crucible B1, is returned to the initial position to be ready for the next operation.

Figure 7:
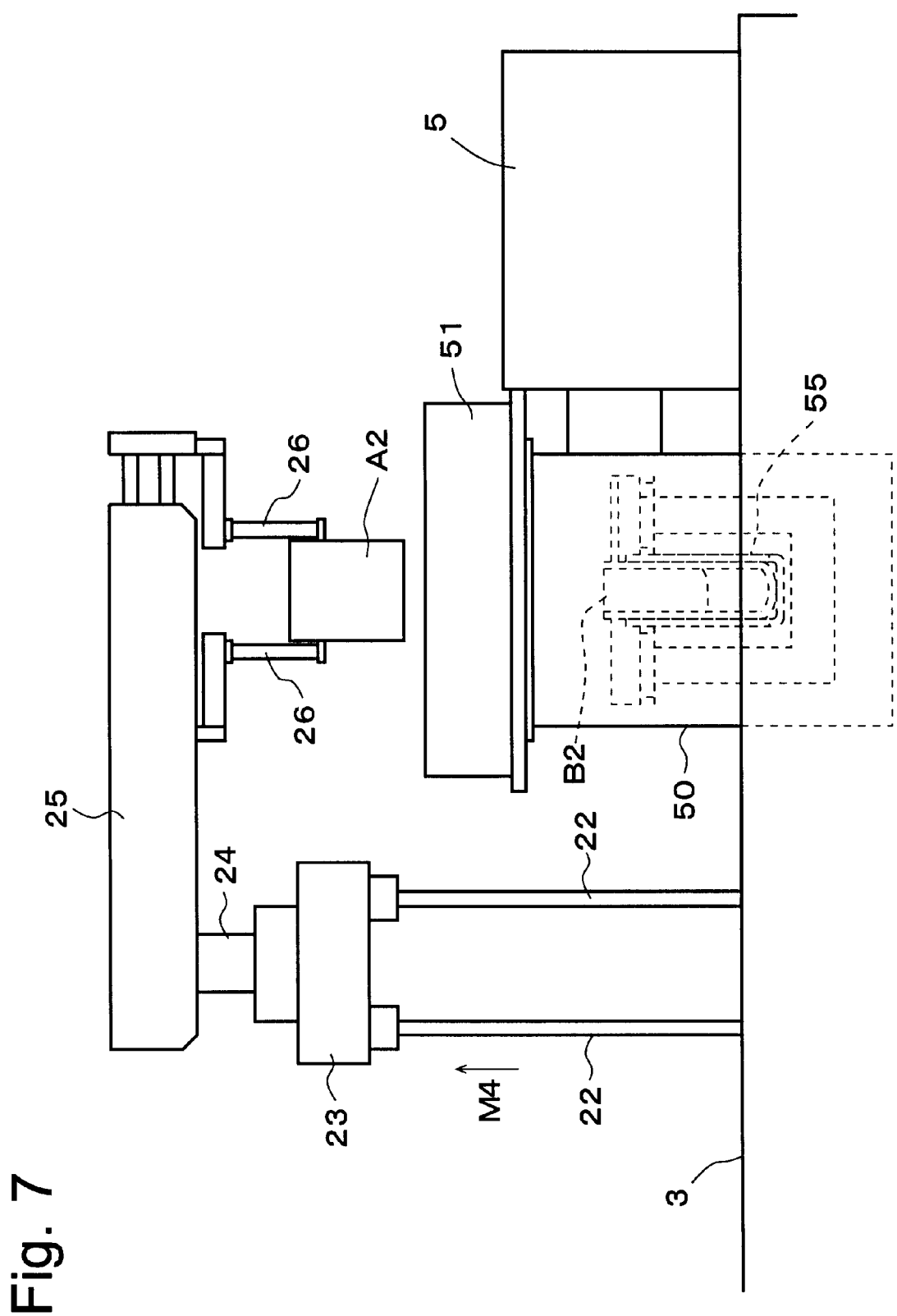
FIG. 7 shows the construction of the ring conveyer E and the casting unit H, as viewed from the right side in FIG. 1.

After the lapse of a preset time period, the metal ingots are adequately melted for the casting work, the ring A2 is conveyed from the burning unit G to the casting unit H. That is, the lifting stage 44 of the burning unit G is lowered to the lowest level with the ring A2 placed on itself. The arm mechanism 20 holds the ring A2, moves along the guide 27 and places the ring A2 on the crucible B2 in the container 50 (FIG. 7). After the arm 25 has been rotated away from the container 50, the cover lifting part 64 holding the cover 60 is lowered. The cover lifting part 64 is stopped when the cover 60 has reached the top of the container 50 (FIG. 8).

After that, the gas inlet valve (not shown) is closed, and the vacuum pump is energized, whereby the air in the chamber is removed through the gas passage 59 to the outside (18B in FIG. 18). As the pressure in the chamber decreases, the cover 60 is pressed on the container 50 more tightly, improving the sealing capacity. The ring A2 is urged downward by the pressing part 61, and the sprue gate 82 of the ring A2 and the open top of the crucible B2 face each other, as shown in FIG. 15. During the evacuation of the chamber, the crucible B2 is maintained at the aforementioned melting temperature. The pressure in the chamber is monitored with a pressure sensor (not shown). When the pressure has reached a preset value (−0.1 Mpa, for example), the engaging plate 66 is moved back to resolve the engagement with the hooks 62. After that, the cover lifting part 64 moves upward, leaving the cover 60 closing the open top of the container 50 (FIG. 9).

Next, the motor 58 is energized by a command of the control circuit to make a clockwise rotation of the chamber from the normal position over about 180 degrees (18C in FIG. 18). According to the rotation of the chamber, the wheel 51 gradually rotates as described above, and when the chamber has reached the reversed position, the cover 60 is completely locked. During the rotation, the cover 60 neither falls nor becomes displaced even before the locking, because the cover 60 is tightly pressed on the container 50 as a result of the evacuation of the chamber.

When the molten metal has an adequate fluidity, a certain amount of inclination of the chamber makes the molten metal flow from the inclined crucible B1 into the reservoir 81 of the ring A1. When the chamber has reached the reversed position, or at a proper time point earlier than that, the vacuum pump is stopped, and the gas inlet valve is opened to start the pressurizing process (18D in FIG. 18). As a result, a compressed air or inert gas rapidly flows through the gas passage 59 into the chamber, and the air or gas further flows through the gap between the open top of the crucible B2 and the ring A2 into the reservoir 81. In this process, first, the sprue gate 82 is completely closed by the molten metal supplied from the crucible B2 into the reservoir 81, and then the air or gas flows into the reservoir to press the top of the molten metal. Since the chamber is maintained in the vacuum state until immediately before the introduction of the air or gas, the sprue runner 83 and the cavity 84, being closed by the molten metal, is still in the vacuum state. Therefore, the molten metal existing at the sprue gate 82 is forced through the sprue runner 83 into the cavity 84 by the differential pressure between the reservoir 81 and the cavity 84. The pressurizing process also causes the cover 60 to undergo a strong outward push, which, however, never causes the displacement of the cover 60 because the cover 60 has already been locked before the pressurizing process.

When the chamber has reached the reversed position, the control circuit commands the motor 58 to stop, and the power supply to the heater 54 is also stopped after a preset time period. After the termination of the power supply to the heater 54, the inside of the chamber is naturally cooled, and the molten metal filling the cavity 84 of the ring A2 starts solidifying (18A in FIG. 18). After continuing the pressurizing process for a preset time period to make the molten metal almost solid, the gas inlet valve is closed, and the vacuum pump is energized again, thus making the cover 60 pulled onto the container 50 by the differential pressure.

Then, the motor 58 is again energized by the command of the control circuit to make counterclockwise rotation of the chamber from the reversed position to the normal position. The cover 60 is unlocked in the course of the rotation, which, however, never causes a fall or displacement of the cover 60 because the cover 60 is pulled onto the container 50 as a result of the evacuation of the chamber.

The motor 58 is stopped when the chamber has reached the normal position. After that, the cover lifting part 64 is lowered to the level where the hooks 62 are inserted into the holes 65, pressing the cover 60 on the container 50. As a result of stopping the vacuum pump, the vacuum state of the chamber is gradually broken due to the introduction of air, so that the difference in pressure from the outside pressure decreases. After the pressure difference has been adequately small, the cover lifting part 64, with the plate 65 being engaged with the hooks 62, moves upward to pull the cover 60 to open the chamber. After that, the arm mechanism 20 operates to hold the processed ring and conveys it to a preset position on the ring-placing platform C. Also, the arm mechanism 30 operates to take the crucible out of the container 50 and returns it to the crucible-placing platform D.

Next, the casting operation on the second piece of ring, ready for use in the furnace 45, is carried out. That is, the arm mechanism 30 holds the second crucible B1 on the crucible-placing platform D and puts it into the container 50. After the metal ingots in the crucible has been adequately melted in the container 50, the arm mechanism 20 conveys the ring A2 from the furnace 45 onto the crucible B2. After that, the casting process is carried out on the second ring in the same manner as on the first ring, as described above.

With the apparatus 1 of this embodiment, the casting of three to five pieces of rings can be carried out basically in the same manner as described above. As can be obviously understood from FIG. 17, it is the burning of the ring that requires the longest time in the whole process. Accordingly, the control sequence may be preferably determined so that each of the two furnaces 44 and 45 is supplied with the rings without a break so that the casting of all the rings is completed most efficiently (i.e. in the shortest time).

After the ring placed on the ring-placing platform C has adequately cooled down, the operator pulls the mold out of the metallic ring 80, and takes out the cast, i.e. the dental prosthesis, by breaking the mold.

It should be noted that the above embodiment is a mere example of the present invention, which can be modified or changed within the scope of the invention.

What is claimed is:

1. An apparatus for casting dental prosthesis comprising:
   a) a ring-placing platform on which a cylindrical ring with a casting model of a thermally subliming material concealed inside may be placed;
   b) a burning unit including a lifting stage and a furnace for heating the cylindrical ring with the casting model to form a mold, where the furnace covers the top of the lifting stage when the lifting stage is lifted to a preset level;
   c) a crucible-placing platform on which a crucible containing a casting material may be placed;
   d) a casting unit including a chamber having a cylindrical container rotatable about a horizontal axis and a cover for closing an open top of the container, a cover mechanism for attaching and detaching the cover to and from the top of the container, a heater for supplying heat to the container to melt the casting material in the crucible when the crucible is put in the container and the mold is positioned over the crucible so that the sprue of the mold faces an open top of the crucible, and a chamber driver for rotating the chamber about the horizontal axis after the casting material has been melted;
   e) a ring conveyer for holding the ring on the ring-placing platform and conveying the ring onto the lifting stage of the burning unit, for holding the ring after burning and positioning the ring over the crucible contained in the container of the casting unit, and for holding the ring after a casting process and returning the ring to the ring-placing platform;
   f) a crucible conveyer for holding the crucible on the crucible-placing platform and conveying the ring into the container of the casting unit, and for taking the crucible out of the container and returning the crucible to the crucible-placing platform; and
   g) a controller for controlling the burning unit, casting unit, ring conveyer and crucible conveyer so that heating of the ring for a preset time period, heating of the crucible and casting work are performed according to a preset sequence.

2. The apparatus according to claim 1, wherein:
   the cover mechanism includes a cover-securing mechanism for allowing vertical attaching/detaching movements of the cover when the chamber is in a normal position, while securing the cover to prevent it from falling off the container when the chamber is turned upside-down; where
   the cover-securing mechanism includes a wheel attached to the upper end of the container;
   the wheel has teeth formed at least at a part of the outer circumference and a stopper projecting from the inner circumference;
   plural projections are formed at preset angular intervals around the horizontal axis at a part where the projections engage with the teeth of the wheel; and
   the cover has a notch that comes to the same position as the stopper when the chamber is in the normal position.

3. The apparatus according to claim 1, wherein each of the ring conveyer and the crucible conveyer includes:
   an arm having a gripper for holding an object;
   a rotating mechanism for rotating the arm about a vertical axis;
   a lifting mechanism for vertically moving the arm; and
   a moving mechanism for moving the arm along a horizontal linear path, where the moving mechanisms of the both conveyers commonly include a guide along which the arms are moved.

4. The apparatus according to claim 3, wherein the ring-placing platform and the burning unit are disposed across the guide, and the crucible-placing platform and the casting unit are disposed across the guide.

* * * * *